United States Patent
Klein

(10) Patent No.: US 10,596,258 B2
(45) Date of Patent: Mar. 24, 2020

(54) METHOD FOR BINDING ACTIVE AGENTS TO ACTIVATED AUTOLOGOUS BLOOD NOSODES AND DEVICE FOR PERFORMING SAID METHOD

(71) Applicant: YENO FOUNDATION AG, Wakefield (GB)

(72) Inventor: Claudia Bettina Klein, Backnang (DE)

(73) Assignee: Yeno Awareness BV, Amsterdam (NL)

( * ) Notice: Subject to any disclaimer, the term of this patent is extended or adjusted under 35 U.S.C. 154(b) by 209 days.

(21) Appl. No.: 15/537,726

(22) PCT Filed: Sep. 10, 2015

(86) PCT No.: PCT/EP2015/001827
§ 371 (c)(1),
(2) Date: Jun. 19, 2017

(87) PCT Pub. No.: WO2016/037705
PCT Pub. Date: Mar. 17, 2016

(65) Prior Publication Data
US 2019/0000972 A1  Jan. 3, 2019

(30) Foreign Application Priority Data

Sep. 11, 2014 (EP) .............................. 20140184416

(51) Int. Cl.
| | | |
|---|---|---|
| *A61K 41/00* | (2006.01) | |
| *A61K 47/64* | (2017.01) | |
| *B01L 1/00* | (2006.01) | |
| *B01L 9/06* | (2006.01) | |
| *B01L 3/00* | (2006.01) | |
| *A61K 31/417* | (2006.01) | |
| *A61K 33/10* | (2006.01) | |
| *A61K 33/24* | (2019.01) | |
| *A61K 33/42* | (2006.01) | |
| *A61K 39/085* | (2006.01) | |
| *A61K 33/16* | (2006.01) | |
| *A61K 39/245* | (2006.01) | |
| *A61K 39/12* | (2006.01) | |
| *A61K 33/06* | (2006.01) | |
| *A61K 33/28* | (2006.01) | |

(52) U.S. Cl.
CPC ........ *A61K 41/0004* (2013.01); *A61K 31/417* (2013.01); *A61K 33/06* (2013.01); *A61K 33/10* (2013.01); *A61K 33/16* (2013.01); *A61K 33/24* (2013.01); *A61K 33/28* (2013.01); *A61K 33/42* (2013.01); *A61K 39/085* (2013.01); *A61K 39/12* (2013.01); *A61K 39/245* (2013.01); *A61K 47/643* (2017.08); *B01L 1/00* (2013.01); *B01L 3/5082* (2013.01); *B01L 9/06* (2013.01); *B01L 2300/06* (2013.01); *B01L 2300/0832* (2013.01); *B01L 2400/043* (2013.01); *B01L 2400/0436* (2013.01)

(58) Field of Classification Search
None
See application file for complete search history.

(56) References Cited

U.S. PATENT DOCUMENTS

2009/0016993 A1 * 1/2009 Rajesh .................. A61K 35/76
424/93.6

FOREIGN PATENT DOCUMENTS

| DE | 10256231 A1 | 8/2003 |
|---|---|---|
| EP | 1596938 A1 | 11/2005 |
| RU | 2305414 C2 | 9/2007 |

OTHER PUBLICATIONS

Hirt, Hans-Dieter; et al; "Preparation of Autologous Blood Nosodes in the Pharmacy [Herstellung von Eigenblutnosoden in der Apotheker]" Deutsche Apotheker Zeitung, 19, 62-65, 2007 (Year: 2007).*
Wiesenauer, Markus; "Treatment with Autologous Blood Nosodes [Die Behandlung Mit Eigenblutnosoden]" Deutche Apothekar Zeitung, Deutscher Apotheker Verlag, Stuttgart, 147, 58-61, 2007 (Year: 2007).*

(Continued)

*Primary Examiner* — David W Berke-Schlessel
(74) *Attorney, Agent, or Firm* — Frost Brown Todd LLP

(57) ABSTRACT

A method for binding an active substance or an active agent to an activated autologous blood nosode comprises a) dissolving blood of a patient in an aqueous or aqueous/ethanol medium or triturating blood of a patient with an excipient approved for globules according to HAB [Homeopathic Pharmacopoeia] in order to obtain a first mixture; b) activating the first mixture by exposure of the first mixture to magnetic pulses having frequencies of the magnet field periods within a range from approximately 0.01 to approximately 20,0000 Hz and maximum field strengths of 50 µT; c) adding an active substance and/or active agent or one or more active substances and/or active agents to the activated first mixture in order to obtain a second mixture; d) succussing the second mixture by mechanical action, wherein steps c) and d) are conducted under the continuous action of the magnetic pulses, and wherein steps c) and d) can be repeated once or several times; and e) activating the succussed second mixture by further continuous exposure to the magnetic pulses and by irradiation with visible light of changing colors produced by LEDs into the succussed second mixture, whereby an increase of the binding capacity of the HSA [human serum albumin] in the blood to the active substance(s) and/or to at least some of the active agent or active agents is achieved. A device for performing the method is also described.

19 Claims, 3 Drawing Sheets

(56) References Cited

OTHER PUBLICATIONS

K. Münnemann et al. "Physics, Chemistry, Biology and Medicine: Spotlight on the Spin." http://www.mpip-mainz.mpg.de/20689/research_report_1179941?c=22413, accessed Dec. 13, 2017.
H. Kerstin et al. "Therapeutic Effects of Whole-Body Devices Applying Pulsed Electromagnetic Fields (PEMF): A Systematic Literature Review," Bioelectromagnetics, vol. 33, No. 2, Feb. 21, 2012, pp. 95-105.
International Search Report and Written Opinion for International PCT Application No. PCT/EP2015/001827, dated Nov. 20, 2015.

* cited by examiner

METHOD FOR BINDING ACTIVE AGENTS TO ACTIVATED AUTOLOGOUS BLOOD NOSODES AND DEVICE FOR PERFORMING SAID METHOD

FIELD OF THE INVENTION

The field of the invention relates to a method for binding of active agents to activated autologous blood nosodes and to a device for performing the method.

BACKGROUND OF THE INVENTION

Autologous blood therapy is now known to broad circles of the population, not lastly since it is included in the list of prohibited doping agents. In autologous blood therapy, blood is removed from the patient and reinjected at another site of the body of the patient. In this context, variants also exist, such as irradiation of the blood with UV-C light, enrichment of the blood with an ozone-oxygen mixture, or addition of nosodes, other homeopathic preparations or immunostimulants such as *Echinacea*, before the reinjection of the blood into the patient.

Less known are the so-called autologous blood nosodes (also referred to as autologous blood therapy according to Imhäuser). For the preparation thereof, a drop of blood taken from the tip of the finger or the earlobe is usually diluted with aqueous ethanol (for example, 10 or 20 mL), or also triturated with sucrose or xylitol, for example, and processed to form globules, and the resulting dispersion or globules is/are administered back to the patient orally at dosages of several drops respectively per day. This first dilution can be diluted further according to the principles of homeopathy, both in the form of a solution and also in the form of globules. The autologous blood nosodes are preferably administered, for example, in allergic and skin diseases as well as in recurring infectious diseases. It is assumed that the mechanism of action is a nonspecific general regeneration reaction.

It is known that blood is composed of erythrocytes, leukocytes, thrombocytes and blood plasma, wherein the last-mentioned blood plasma consists of approximately 90% water and approximately 10% substances dissolved therein, mainly salts and buffers (acids/bases) as well as proteins (for example, albumin and coagulation factors).

The key protein, albumin (or human serum albumin (HSA)), is used primarily for maintaining the osmotic pressure of the blood as well as for the transport of water-insoluble substances in the blood. Furthermore, it has a disintegrating action on erythrocytes and thrombocytes. HSA is an amphoteric protein having a molecular weight of approximately 66.470 Da. It has an elliptical shape with a relatively hard core and a flexible surface structure (Münnemann, Kerstin; Hinderberger, Dariush; Research Report from Webservice 2011—Max-Planck Institute for Polymer Research, Report No. 1179941, which is available on the worldwide web at mpip-mainz.mpg.de).

In medicine, it has been known for some time that binding of drugs to HSA can entail considerable advantages, for example, a reduction of the required active substance quantity, fewer side effects, and a more targeted transport of the active substance to the site of the disease process. Here, the binding of the active substance to the HSA occurs either by covalent bond (for example, methotrexate-HSA or aminopterin-HSA) or, in the case of nab (nanoparticle albumin-bound)-paclitaxel, by high-pressure homogenization of amorphous paclitaxel in the presence of HSA to form a colloidal nanoparticle suspension.

Normal nosodes (that is to say non-autologous blood nosodes), the name of which is derived from the Greek word "nosos" ("disease"), are produced according to procedures of the HAB (Homeopathic Pharmacopoeia) from (greatly weakened or killed) pathogens, pathological materials such as blood of a sick person, pus, or cells from organs, for example, cancer cells, or body secretions or excretions including, for example, hormones (today, more than 2000 nosodes are commercially available). In the nosode, the principle of immunization (stimulation of the body's self-healing forces by exposing the body to a weakened disease stimulus) is associated with the principle of homeopathy. The term "nosode" was coined around 1830 by the American physician Constantin Hering. However, the principle has been known since antiquity. In 800 BC, the Chinese already used diluted smallpox secretions which were introduced through a scratch under the skin against the disease. Hippocrates as well taught to "heal bad with bad," and the British philosopher and physician Robert Fludd described the treatment of consumptive patients with dilutions of their sputum.

It was the aim of the invention to combine the advantages of an autologous nosode with the advantages of binding an active substance or active agent to HSA, i.e., to load the HSA present in the autologous blood nosode with an active substance or active agent, in particular in an effective but as mild as possible a manner.

SUMMARY OF THE INVENTION

The invention relates to a method for binding an active substance or an active agent to an activated homologous blood nosode, comprising:

a) dissolving blood of a patient in an aqueous or aqueous/ethanol medium or triturating blood of a patient with an excipient approved for globules according to HAB in order to obtain a first mixture;

b) activating the first mixture by exposure of the first mixture to magnetic pulses having frequencies of the magnet field periods within a range from approximately 0.01 to approximately 20,0000 Hz and maximum field strengths of 50 µT in order to obtain an activated first mixture;

c) adding an active substance and/or active agent or one or more active substances and/or active agents to the activated first mixture in order to obtain a second mixture;

d) succussing the second mixture by mechanical action, wherein steps c) and d) are conducted under the continuous action of the magnetic pulses, and wherein steps c) and d) can be repeated once or several times, as a result of which a succussed second mixture is obtained; and e) activating the succussed second mixture by the further continuous exposure to the magnetic pulses and by irradiation with visible light of changing colors produced by LEDs into the succussed second mixture, whereby an increase of the binding capacity of the human serum albumin (HSA) in the blood to the active substance(s) and/or to at least some of the active agent or active agents is achieved and a modified autologous blood nosode is obtained.

The invention further relates to a device for performing the method according to the invention, comprising:

1) a closable housing, 2) a sample holder arranged in the housing, which can hold a transparent vessel in which the first mixture of step a) or b) is produced or contained, 3) a device which can repeatedly bring about a mechanical percussing and/or translation movement of the vessel, 4) a magnetic coil which can generate magnetic pulses directed onto the vessel and having frequencies of the magnetic field periods in the range from approximately 0.01 to approximately 20,0000 Hz and maximum field strengths of 50 µT; and 5) a device which comprises LEDs which can generate visible light of at least two colors and can irradiate the generated light into the vessel.

DETAILED DESCRIPTION

Figure 1:
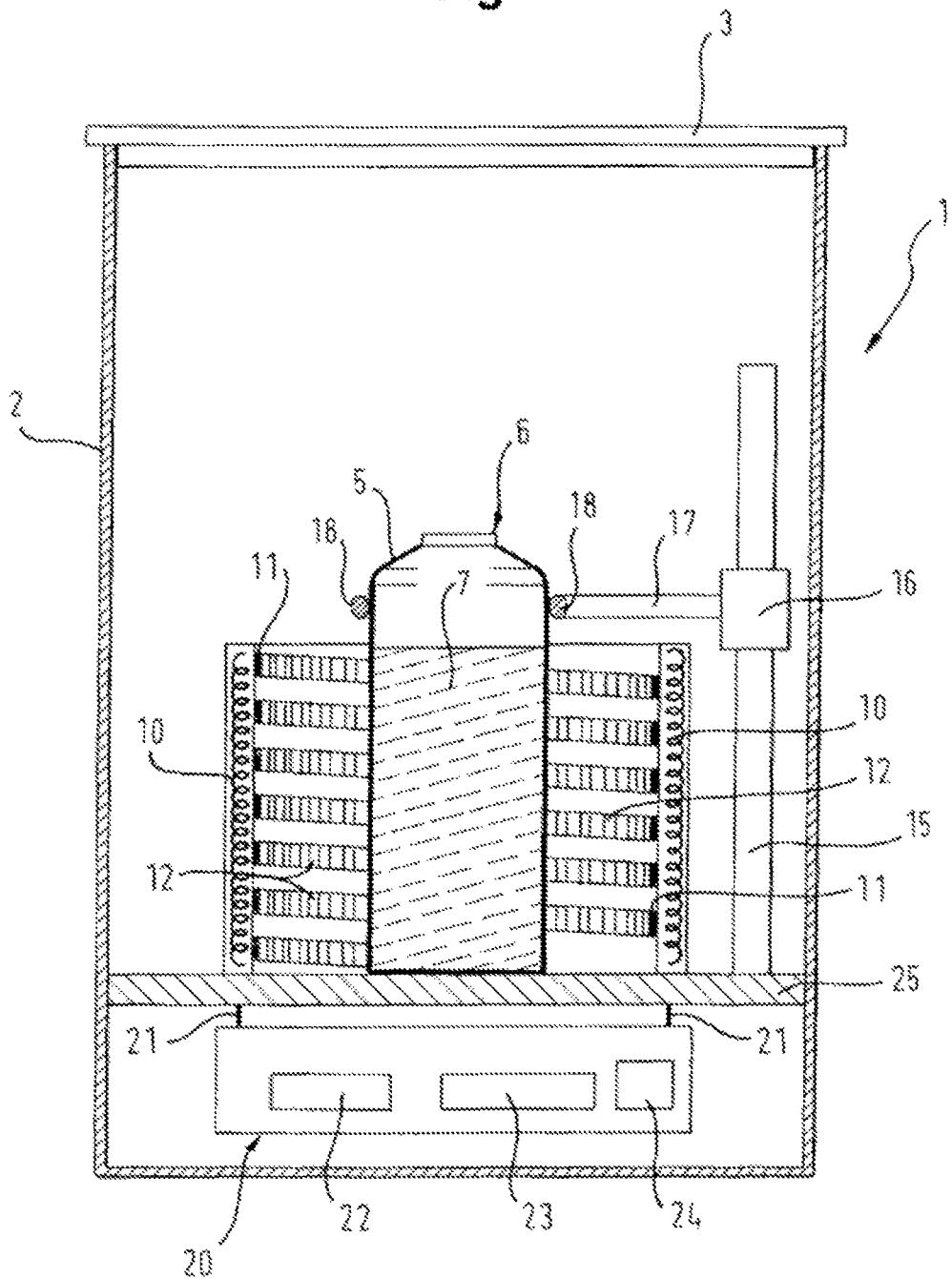
FIG. 1 shows a diagrammatic cross-sectional view along line a-a of FIG. 2 of an embodiment of a device according to the invention.

The autologous blood nosode used in the invention is preferably a suspension of one drop to 3 mL, preferably 2 mL of blood in 0.5 mL to 20 mL, preferably 1 mL to 10 mL of 40 to 85 vol % ethanol, for example, 0.5 mL of blood in 2 mL of 70% ethanol or 2 mL of blood in 5 mL of 70% ethanol. But in the case of alcohol intolerance of the patient and in children, a physiological saline solution (0.9% NaCl solution) or conventional solid globule carrier substances such as sucrose or xylitol can also be used for the dilution.

This autologous blood nosode is activated by magnetic pulses within a frequency range from 0.01 to 20,000 Hz and with a maximum magnetic field strength up to 50 µT. The pulses are preferably so-called needle pulses and have, for example, a saw-tooth form. Frequently, needle pulse packets of similar form but varying field strength are used; for example, several successive pulse packets of similar form but varying field strength can be used for a time period of, for example, approximately 10 to approximately 20 µs and with a pause between the pulse packets of approximately 55 to approximately 75 µs. Suitable magnetic pulses are supplied, for example, by a vita-Life®-R-Magnetstab [magnetic rod] (available from VITA LIFE HandelsgmbH, Gewerbepark1, 9220, Velden-Lind, Austria). The first activation occurs preferably for a time period of approximately 0.5 to approximately 10 minutes, for example, for approximately 1 or 2 to approximately 5 minutes.

It is known that pulsed magnetic fields of appropriate frequency have effects on blood. This is well-documented for the case of iron-containing erythrocytes, but the other charge-containing or polarizable blood components are also influenced by the magnetic fields. It is assumed that, in the case of HSA, which has numerous positively and negatively charged molecule portions, the conformation of the molecule is influenced by the magnetic pulses.

The active substances and active agents that are added to the activated autologous blood nosode can be selected from normal nosodes, normal homeopathic agents (both referred to here as "active agents") as well as from allopathic active substances (active substances that occur in nature as well as those made of synthetic active substances). The selection is based on the clinical picture of the patient and is determined by the treating therapist. Allopathic active substances are added in only very small amounts, so that, to the extent possible, the transport capacity of the HSA in the autologous blood nosode is not exceeded.

To mention only a few examples, it is possible to add, as homeopathic active agents,
Hepar Comp (company Heel),
Hypophysis/Stannum (company Wala), and
Cuorum Injectopas (company Pascoe);
as nosodes,
TBE C30,
Herpes Zoster Injeel (company Heel),
Herpes vulgaris Injeel (company Heel),
Sanukehl® Staph D5/*Staphylococcus aureus* D5 ampules, and
EBV C30,
and, as allopathic active substances,
alpha-lipoic acid, 600 mg
Folic acid Forte Hevert; in a quantity of 20 mg
Pyridoxin hydrochloride (vitamin B6); in a quantity of 25 mg, and
Regeneresen (RNA Frischzellen [fresh cells], company Dyckerhoff Pharma),
to the autologous blood nosode.

Usually, up to four active agents or active substances are added to the autologous blood nosode, before the step of mechanical action is carried out. However, in special cases, a mechanical action can also be applied after each addition, before the further activation step with light is carried out.

The mixing of the activated autologous blood nosode with the active substances/active agents occurs by means of a brief mechanical action, for example, percussing of the vessel ("tapping") or, for example, in the case of fresh cells, repeated rapid translation movements of the vessel ("shaking"). Preferably, the brief mechanical percussions or the brief translation movement of the vessel is carried out approximately 20 to approximately 150 times (depending on the admixed active substance/active agent).

The mixture thus obtained or modified autologous blood nosode is further activated by magnetic pulses, in the same manner as described above for the starting autologous blood nosode, and additionally irradiated with visible light of alternating colors generated by LEDs, for example, with two or more, preferably three or four or more, more preferably five or six or even more colors, in general for approximately 0.5 to approximately 10 minutes, for example, for approximately 1 to approximately 5 minutes, and furthermore preferably with a luminosity in the range from 3000 to 5000 mcd, for example, of 4000 mcd. From complementary medicine, it is known that monochromatic light in the visible range has multifaceted effects on blood, one of them being the increase of the binding capacity of HSA. In addition to the above-described magnetic pulses, which are also used during the light irradiation, the light can be led through a magnetic field downstream of the LEDs, which has a magnetic field strength of approximately 50 µT, and which, furthermore, can also be modulated by additional magnetic pulses having, for example, a field strength of 20 µT with frequencies, for example, in the range of 120-140 Hz and of approximately 90 kHz. A device with suitable LEDs, which also comprises a permanent magnet and a magnetic coil for generating suitable permanent and pulsed magnetic fields can be obtained under the commercial name FW-Pen by Professor Schaack, CE, Helzel Messtechnik GmbH, Carl-Benz-Straße 9, D-24568 Kaltenkirchen.

The above-described steps of adding an active substance/active agent or one or more active agents/active substances can be repeated with the initially prepared autologous blood nosode up to six or seven times, preferably up to four times.

In the autologous blood nosode, which has been modified as described above with an active substance/active agent or with one or more active substances/active agents and activated with magnetic pulses and light, the active substances/active agents (or at least some of the active agents) are in close association with HSA. This ensures that they are properly transported to the site where their action is desired.

A device for carrying out the above-explained method according to the invention comprises:

a) a closable housing, b) a sample holder arranged in the housing, which can hold a transparent vessel in which the first mixture of step a) or b) is produced or contained, c) a device which can repeatedly bring about a mechanical percussing and/or translation movement of the vessel, d) a magnetic coil which can generate magnetic pulses directed onto the vessel and having frequencies of the magnetic field periods in the range from approximately 0.01 to approximately 20,0000 Hz and maximum field strengths of 50 µT; and e) a device which comprises LEDs which can generate visible light of different colors and irradiate the generated light into the vessel.

The housing can be any closable metal or plastic housing.

The transparent vessel can comprise a septum, which is removable, for example, through which the fluids required for the production of the nosode can be injected. Solid substances can be introduced after the removal of the septum.

The sample holder b) is generally a clamp-like device into which the vessel is clamped. It can be designed to be movable so as to perform a pivoting or shaking movement (an alternative of the device c)).

In general, a mechanical percussing of the vessel is also needed. This can be achieved, for example, by a hammer-like tapping device (another alternative of device c)).

In another embodiment, the sample holder and a device which both can ensure a mechanical percussing of the vessel and can also perform a translation movement, are designed to form a single piece. For example, this can be a sample holder which is connected to a lifting device which, for example, can be moved up and down by means of an electric motor on a rod-shaped holder. The downward movement can be associated with a striking of a base, as a result of which the vessel and the content thereof are mechanically percussed.

Moreover, the vessel contains a metal, preferably copper, magnetic coil which, when appropriate electrical currents are run through it, can generate magnetic pulses having frequencies of the magnetic field periods in the range from approximately 0.01 to approximately 20,0000 Hz and maximum field strengths of 50 µT. In a preferred embodiment, the cylinder is arranged cylindrically around the vessel and provided with a magnetically permeable cladding.

Furthermore, the vessel contains LEDs which generate visible light of at least two, preferably at least three or four, more preferably five colors or even more, as well as the mixed colors thereof, and which can irradiate into the transparent vessel. For example, strips that comprise such LEDs are commercially available.

The vessel furthermore contains the power supply required for the mentioned devices as well as devices for controlling these devices optionally by means of an electronic control with a programmed or programmable chip.

On the outside, the vessel can comprise, for example, an on/off switch, a display device, a counter for counting the procedures that have been carried out, a device for setting the number of mechanical percussions or translation movement processes, and a USB connection or another device for reading in data. The operation control for these operation devices is then also contained in the housing.

In addition, the vessel can optionally also contain a permanent magnet which has a permanent magnetic field equal to or weaker than 50 µT.

Figure 2:
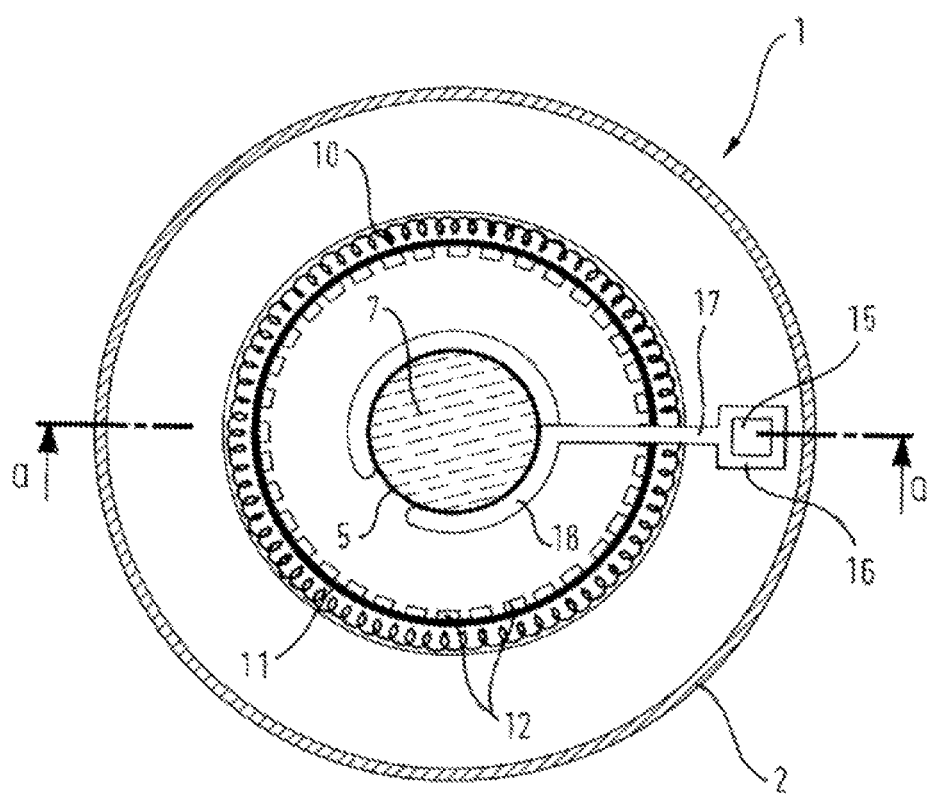
FIG. 2 shows a diagrammatic top view of the device of FIG. 1.
Figure 3:
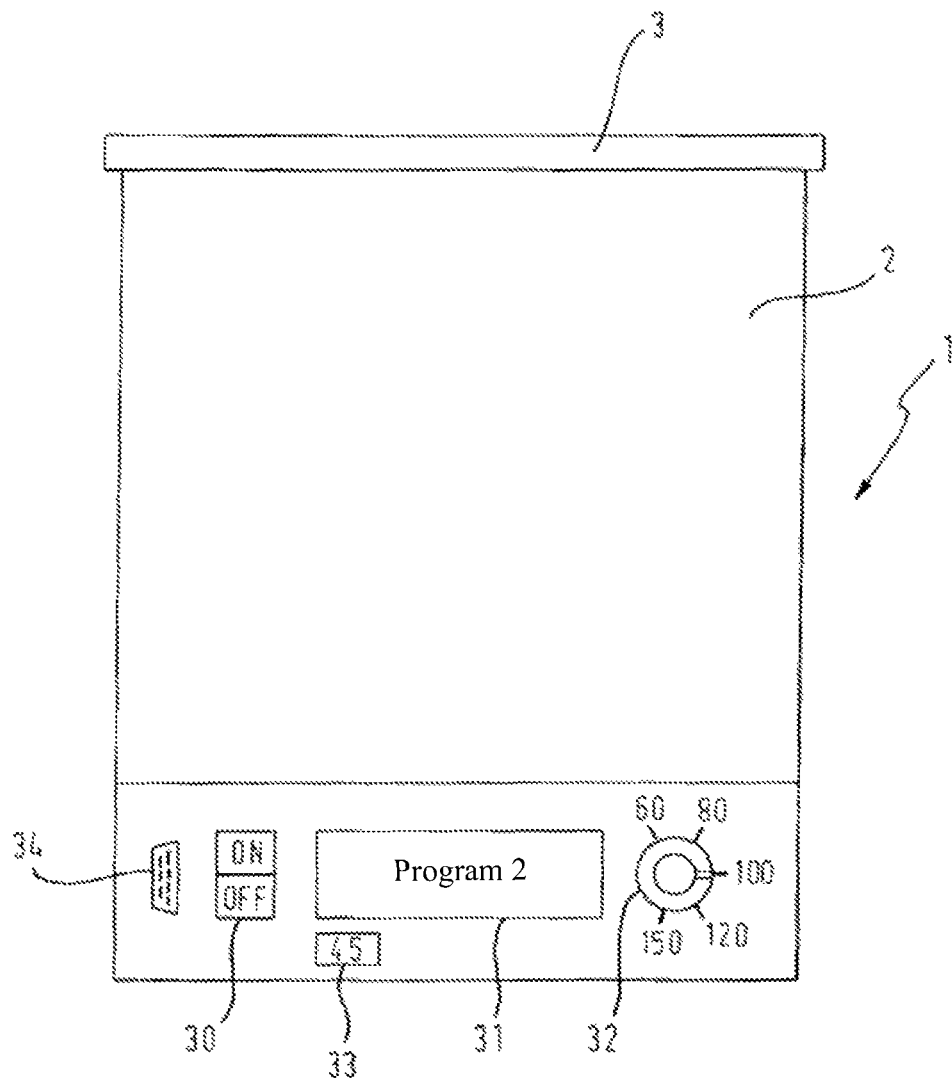
FIG. 3 shows a front plan view of the device of FIG. 1.

FIG. 1 shows a cross-sectional view along line a-a of FIG. 2 of an embodiment of the device 1 according to the invention. In a vessel 2, which can be closed with a lid 3, a transparent vessel (for example, a beaker for preparations) 5, which is provided with a septum 6, is located in a holder 18 which is connected via an arm 17 to a lifting device 16. The lifting device 16 can be moved up and down by means of an electric motor (not shown) on the holder 15, wherein it can be moved downward to the extent that it can allow the vessel to strike an intermediate bottom plate 25.

The transparent vessel is surrounded cylindrically by a plastic-clad copper coil 10 extending from the intermediate bottom plate 25 approximately to a level under the holder 18, when it is located at the lowest point, at or below the level at which the surface of an autologous blood nosode 7 found in the vessel is located.

On the side of the clad coil facing the vessel, an LED strip 11 with LEDs 12 is attached helically, the latter being capable of generating light of five different wavelength ranges in the visible range of the electromagnetic spectrum as well as mixed colors.

The following are located within a control and supply unit 20 under the intermediate bottom plate 25: a power supply 24 which can be connected to the power grid and which, via cable 21, supplies the current to the coil 10, to the LEDs 12 and to the electrical motor for the lifting device 16, an electronic control unit 23 for controlling the coil 10, the LEDs 12 and the electric motor for the lifting device 16, as well as an operation control unit 22 for the control of the devices located on the external side of the device, namely a display device 31, a device 32 for setting the number of the movements of the lifting device 16, an on/off switch 30, a counter 33 for the number of procedures that have been carried out in the device, and a USB connection 34.

EXAMPLES

Example 1: Patient Mr. H. From Frankfurt, Age Group 1936

A) Disease Picture

In this patient, shortly after a TBE [tick-borne encephalitis] vaccination, full body eczema with severe pruritus occurred. A 6-week medical treatment with various allopathic means, including cortisone ointments, led to no improvement at all.

B) Nosode Preparation on Jun. 9, 2014

0.5 mL of blood of the patient were dissolved in a beaker for preparations with 5 mL of 70% ethanol solution and activated for 5 minutes magnetically with a vita-Life®-R-Magnetstab (available from VITA LIFE HandelsgmbH, Gewerbepark1, 9220, Velden-Lind, Austria). Subsequently, the agents described below were added under further magnetic field activation with the magnetic rod.

| | |
|---|---|
| 30 drops of Q80, company *Calendula* | 0.5 mL |
| 10 globules of TBE Nosode C30 | 0.5 mL |
| 1 ampule of Hypophysis/Stannum | 1.0 mL |

The mixture was then succussed under continuous magnetic field activation by allowing the beaker for preparations to strike a base 120 times, and was irradiated for 1 minute with an FW-Pen by Professor Schaack, CE (Helzel Messtechnik GmbH, Carl-Benz-Straße 9, D-24568 Kaltenkirchen).

A second addition of drugs occurred as follows:

| | |
|---|---|
| 1 ampule of Histamin Injeel Heel | 2.0 mL |
| 1 ampule of Calcium Carbonicum Injeel Heel | 2.0 mL |
| 1 ampule of Glandula Thymi Injeel Heel | 2.0 mL |
| 1 ampule of Coenzympe Comp. | 2.0 mL |
| Total volume of the drugs added | 10 mL |

Then, the modified final autologous blood nosode was succussed under further continuous magnetic field activation by allowing the beaker for preparations to strike a base 100 times and was irradiated again for 1 minute with an FW-Pen by Professor Schaack, CE (Helzel Messtechnik GmbH, Carl-Benz-Straße 9, D-24568 Kaltenkirchen).

C) Intake of the Modified Autologous Blood Nosode

The modified autologous blood nosode prepared as described above was administered orally to the patient, 3 times 10 drops daily, for a period of 5 days. In the process, the nosode had to remain in the mouth (insalivation) for 2 minutes without swallowing.

D) Treatment Result According to Patient Statement

After a few hours, the patient already no longer had pruritus. A clear healing of the eczema started already on the second day after the nosode intake. After one week, the eczema had healed nearly completely. The patient is now undergoing a follow-up therapy (biological regeneration medicine according to C. Klein).

Example 2: Patient Mrs. M. From Remshalden, Age Group 1942

A) Disease Picture

The patient had bronchial asthma and pulmonary emphysema with severe respiration restriction due to removal of right lung segments 15 years ago. Only ⅓ of the right lung remained.

Her allopathic medication consisted of:

Viani mite 50/100

Spiriva

B) Nosode Preparation on Jun. 21, 2014

0.5 mL of blood of the patient were dissolved in a beaker for preparations with 5 mL of 70% ethanol solution and activated for 5 minutes magnetically with a vita-Life®-R-Magnetstab (available from VITA LIFE HandelsgmbH, Gewerbepark1, 9220, Velden-Lind, Austria). Subsequently, the agents described below were added under continued magnetic field activation with the magnetic rod.

| | |
|---|---|
| 20 drops of deionized Phosphorus D6 | 0.5 mL |
| 15 drops of Atem, company *Calendula* | 0.5 mL |
| 3 ampules of N. Vagus GI D6 Wala | 3 × 2 mL = 6.0 mL |

The mixture was then succussed under continuous magnetic field activation by allowing the beaker for preparations to strike a base 150 times, and was irradiated for 1 minute with an FW-Pen by Professor Schaack, CE (Helzel Messtechnik GmbH, Carl-Benz-Straße 9, D-24568 Kaltenkirchen).

A second addition of drugs occurred as follows:

| | |
|---|---|
| 2 ampules of Injectio antiasthmatica Injeel Heel | 2 × 1 mL = 2.0 mL |
| 2 ampules of Medulla oblongata Injeel Heel | 2 × 2 mL = 4.0 mL |

This resulting mixture was then succussed under further continuous magnetic field activation by allowing the beaker for preparations to strike a base 100 times, and was irradiated again for 1 minute with an FW-Pen by Professor Schaack, CE (Helzel Messtechnik GmbH, Carl-Benz-Straße 9, D-24568 Kaltenkirchen).

A third addition of drugs occurred as follows:

| | |
|---|---|
| 2 ampules of Bronchus suis Injeel Heel | 2 × 2 mL = 4.0 mL |
| 1 ampule of Hypothalamus suis Injeel Heel | 2.0 mL |

This resulting mixture was then succussed under further continuous magnetic field activation by allowing the beaker for preparations to strike a base 150 times, and was irradiated again for 1 minute with an FW-Pen by Professor Schaack, CE (Helzel Messtechnik GmbH, Carl-Benz-Straße 9, D-24568 Kaltenkirchen).

A fourth and last addition of drugs occurred as follows:

| | |
|---|---|
| 1 ampule of Glandula Thymi suis Injeel Heel | 2.0 mL |
| 1 ampule of ATP Heel | 2.0 mL |
| 12 drops of Lebensfreude, company *Calendula* | 0.5 mL |
| 5 drops of Colchicum Hevert | 0.5 mL |
| Total volume of the added drug | 24 mL |

The modified final autologous blood nosode thus obtained was then succussed under further continuous magnetic field activation by allowing the beaker for preparations to strike a base 150 times, and was irradiated again for 1 minute with an FW-Pen by Professor Schaack, CE (Helzel Messtechnik GmbH, Carl-Benz-Straße 9, D-24568 Kaltenkirchen).).

C) Intake of the Modified Autologous Blood Nosode

The modified autologous blood nosode prepared as described above was administered orally to the patient, 5 times 10 drops daily, for a period of 14 days. In the process, the nosode had to remain in the mouth for 2 minutes (insalivation) without swallowing.

For the nosode, 1 spray of Spenglersan Kolloid T from Meckel was given in each case in the left and right crook of the arm.

D) Treatment Result According to Medical Observation and Statement of the Patient 5 minutes after the intake of the nosode, a clear improvement of the respiration could already be observed. After 1 hour, the patient explained that she was able to climb stairs without other respiration problems, without having to stop. Overall she feels almost free of discomfort and fitter. The absence of discomfort has continued for the last 14 days; based on the evaluation of the patient there is an approximately 80% improvement of respiration and physical fitness compared to the previous state.

The patient is now receiving a follow-up therapy (biological regeneration medicine according to C. Klein) with administration of a second nosode.

Example 3: Patient Mr. F. From Berlin, Age Group 1997

A) Disease Picture

For the past 3 months the patient had had ear pains with a sensation of pressure as well as right-side swallowing difficulties. Serological results were available. The antibiotics prescribed by the family doctor led to no improvement. A subsequent, corresponding dysbiosis management was instituted and carried out.

B) Nosode Preparation on May 21, 2014

0.5 mL of blood of the patient were dissolved in a beaker for preparations with 5 mL of 70% ethanol solution and activated for 5 minutes magnetically with a vita-Life®-R-Magnetstab (available from VITA LIFE HandelsgmbH, Gewerbepark1, 9220, Velden-Lind, Austria). Subsequently, the agents described below were added under further magnetic field activation with the magnetic rod.

| | |
|---|---|
| 10 drops of EBV Nosode C30 | 0.5 mL |
| 10 drops of Sanukehl Staphylokokken [*Staphylococci*] D6 | 0.5 mL |
| 10 drops of ion. Fluorine D6 | 0.5 mL |

The mixture was then succussed under continuous magnetic field activation by allowing the beaker for preparations to strike a base 100 times, and was irradiated for 1 minute with an FW-Pen by Professor Schaack, CE (Helzel Messtechnik GmbH, Carl-Benz-Straße 9, D-24568 Kaltenkirchen).

A second addition of drugs occurred as follows:

| | |
|---|---|
| 1 ampule of Folsäure [Folic acid] forte Hevert | 2.0 mL |
| 1 ampule of Hypophysis/Stannum | 1.0 mL |
| 20 drops of Q80, company *Calendula* | 0.5 mL |

This resulting mixture was then succussed under further continuous magnetic field activation by allowing the beaker for preparations to strike a base 100 times, and was irradiated again for 1 minute with an FW-Pen by Professor Schaack, CE (Helzel Messtechnik GmbH, Carl-Benz-Straße 9, D-24568 Kaltenkirchen).

A third addition of drugs occurred as follows:

| | |
|---|---|
| 2 ampules of Para-Benzochinon, company Heel | 4.0 mL |
| 1 ampule of N. Vagus GI D6 Wala | 2.0 mL |

This resulting mixture was then succussed under further continuous magnetic field activation by allowing the beaker for preparations to strike a base 100 times, and was irradiated again for 1 minute with an FW-Pen by Professor Schaack, CE (Helzel Messtechnik GmbH, Carl-Benz-Straße 9, D-24568 Kaltenkirchen).

A fourth and last addition of drugs occurred as follows:

| | |
|---|---|
| 10 drops of Regenaplex 102 | 0.5 mL |
| 10 globules of *Arnica* C30 | 0.0 mL |
| Total volume of the added drugs | 11.5 mL |

The modified autologous blood nosode thus obtained was then succussed under further continuous magnetic field activation by allowing the beaker for preparations to strike a base 100 times, and was irradiated again for 1 minute with an FW-Pen by Professor Schaack, CE (Helzel Messtechnik GmbH, Carl-Benz-Straße 9, D-24568 Kaltenkirchen), and, in the end, it was filled to 25 mL with 70% ethanol to obtain the modified final autologous blood nosode.

C) Intake of the Modified Autologous Blood Nosode

The modified autologous blood nosode prepared as described above was administered orally to the patient, 3 times 15 drops daily, for a period of 3 days. In the process, the nosode had to remain in the mouth for 2 minutes (insalivation) without swallowing.

D) Treatment Result According to Statements of the Patient 5 minutes after the intake of the nosode, he already observed a very clear to complete cessation of the sensation of pressure on the ears, as well as abatement of the swallowing difficulties. According to the statement of the patient, there was no further discomfort from that time on.

After a few days, tinnitus occurred, presumably caused by the cervical vertebrae. An examination by the otorhinolaryngologist revealed no hearing problem or inflammation. The patient was then again given an appropriate supportive therapy recommendation. No information on the current state is available.

Example 4: Small Child, 2½ Years

A) Disease Picture

For 2 years, the child had suffered from persistent paralysis symptoms, initially with extreme sleepiness. This occurred 1 day after a 6-in-1 immunization carried out by the pediatrician. Previously, the child had developed normally, and slept and eaten normally. Since the time of the vaccination, the child had to be woken up for eating. Overall, the child's development, including of the feet in particular, had remained delayed. The child presented major general aggression potential (he would lash out and shout) and high muscular tension.

Another pediatrician later prescribed Hypophysis/Stannum globules, whereafter the small child woke up from the sleepiness and found a normal sleep rhythm.

B) Nosode Preparation on May 2, 2014

1 drop of blood of the child was dissolved in 1 mL of physiological saline solution (0.9% NaCl solution) and activated for 5 minutes magnetically with a vita-Life®-R-Magnetstab (available from VITA LIFE HandelsgmbH, Gewerbepark1, 9220, Velden-Lind, Austria). Subsequently, the agents described below were added under continued magnetic activation with the magnetic rod.

| | |
|---|---|
| 5 drops of ionized Fluorine D6 | 0.5 mL |
| 1 ampule of Hypophysis/Stannum, company Wala | 1.0 mL |

The mixture was then succussed under continuous magnetic field activation by allowing the beaker for preparations to strike a base 100 times, and was irradiated for 1 minute with an FW-Pen by Professor Schaack, CE (Helzel Messtechnik GmbH, Carl-Benz-Straße 9, D-24568 Kaltenkirchen).

A second addition of drugs occurred as follows:

| | |
|---|---|
| 1 drop of Atem Elixier, Kalendula Kräutergarten | 0.5 mL |
| 1 ampule of Folsäure forte, company Hevert | 2.0 mL |

This resulting mixture was then succussed under further continuous magnetic field activation by allowing the beaker for preparations to strike a base 100 times, and was irradiated again for 1 minute with an FW-Pen by Professor Schaack, CE (Helzel Messtechnik GmbH, Carl-Benz-Straße 9, D-24568 Kaltenkirchen).

A third addition of drugs occurred as follows:

| | |
|---|---|
| 3 tablets of Mercurius solubilis C6 | 0.0 mL |
| 10 drops of ionized phosphorus D6 | 0.5 mL |
| 10 drops of ionized magnesium D6 | 0.5 mL |

This resulting mixture was then succussed under further continuous magnetic field activation by allowing the beaker for preparations to strike a base 100 times, and was irradiated again for 1 minute with an FW-Pen by Professor Schaack, CE (Helzel Messtechnik GmbH, Carl-Benz-Straße 9, D-24568 Kaltenkirchen).

A fourth addition of drugs occurred as follows:

| | |
|---|---|
| 1 ampule of Cerebrum suis Injeel, company Heel | 2.0 mL |
| 10 drops of Regenaplex No. 109 | 0.5 mL |
| 10 drops of Regenaplex No. 112 | 0.5 mL |
| Total volume of the added drugs: | 8 mL |

The modified autologous blood nosode thus obtained was then succussed under further continuous magnetic field activation by allowing the beaker for preparations to strike a base 100 times, and was irradiated again for 1 minute with an FW-Pen by Professor Schaack, CE (Helzel Messtechnik GmbH, Carl-Benz-Straße 9, D-24568 Kaltenkirchen).

In the end, 2 capsules of 500 mg of L-ornithine each were added, whereby the modified final autologous blood nosode was prepared.

C) Intake of the Modified Autologous Blood Nosode

The modified autologous blood nosode prepared as described above was administered orally to the patient, 3 times 10 drops daily, for a period of 10 days. In the process, the nosode had to remain in the mouth (insalivation) for 2 minutes without swallowing.

D) Treatment Result According to the Statement of the Patient's Mother

After the administration of the nosode, an immediate improvement of the affective state occurred. The child no longer exhibited aggression, a tension reduction was observed, there was further improvement of sleep, regression of the paralysis symptom of the feet and then normal development of the locomotor system. The child can now climb stairs alone and dress himself. Furthermore, since that time he plays with other children in the nursery school, which was not the case before. Overall, a normal development and improvement of speech occurred.

For the nosode therapy, a therapy recommendation of biological regeneration therapy was prescribed. The regeneration therapy included a mineral therapy as well as dysbiosis management.

The mother noted in a letter:

" . . . From the day of the first administration, one could see clear differences compared to before. He no longer has uncontrolled fits of anger! He is much more active and in terms of development he is also making clear progress . . . his nursery school teachers confirm the progress. They say that it is incredible, it is as if he had been exchanged!!! . . . . He talks a lot more and above all better. Plays with other children!! He is no longer so withdrawn . . . in terms of development, he is progressing enormously."

All the published documents cited herein are hereby included with their entire content by reference.

The invention claimed is:

1. A method for binding an active substance or an active agent to an autologous blood nosode, comprising:
    a) obtaining a first mixture by:
        1. dissolving blood of a patient in an aqueous or aqueous/ethanol medium to obtain the first mixture; or
        2. triturating blood of a patient with an excipient to obtain the first mixture;
    b) processing the first mixture by exposure of the first mixture to magnetic pulses generated by a magnetic coil, the magnetic pulses having frequencies of magnet field periods within a range from about 0.01 to about 20,000 Hertz and maximum field strengths of 50 µTesla for at least 10 µs to obtain a processed first mixture;
    c) adding one or more active substances, active agents or mixtures thereof to the processed first mixture to obtain a second mixture;
    d) succussing the second mixture by mechanical action, wherein steps c) and d) are conducted under a continuous action of the magnetic pulses, and wherein steps c) and d) can be repeated once or several times, to obtain a succussed second mixture; and
    e) processing the succussed second mixture by further continuous exposure to the magnetic pulses and by irradiation with visible light of changing colors produced by light emitting diodes into the succussed second mixture, whereby an increase of binding capacity of human serum albumin in the blood to the one or more active substances, active agents or mixtures thereof is achieved and a modified autologous blood nosode is obtained.

2. The method according to claim 1, characterized in that the quantity of the blood is from 1 drop to 2 milliliters, and the blood is dissolved in 1 milliliters to 10 milliliters of 70% by volume aqueous ethanol.

3. The method according to claim 1, wherein the one or more active substances, active agents or mixtures thereof is/are selected from members of the drug group selected from the group consisting of: nosodes, homeopathic drugs, allopathic drugs and combinations thereof.

4. The method according to claim 2, wherein the one or more active substances, active agents or mixtures thereof is/are selected from members of the drug group selected from the group consisting of: nosodes, homeopathic drugs, allopathic drugs and combinations thereof.

5. The method according to claim 1, wherein succussing by mechanical action in step d) is carried out successively from about 20 to about 200 times.

6. The method according to claim 1, wherein succussing by mechanical action in step d) is carried out successively from about 50 to about 150 times.

7. The method according to claim 3, wherein succussing by mechanical action in step d) is carried out successively from about 20 to about 200 times.

8. The method according to claim 4, wherein succussing by mechanical action in step d) is carried out successively from about 20 to about 200 times.

9. The method according claim 1, wherein processing the first mixture by exposure to magnetic pulses comprises exposure to needle pulse packets with pauses in between.

10. The method according claim 2, wherein processing the first mixture by exposure to magnetic pulses comprises exposure to needle pulse packets with pauses in between.

11. The method according to claim 1, wherein the visible light of changing colors produced by the light emitting diodes has a luminosity of about 4,000 millicandelas and the irradiation occurs for about 1 minute to about 5 minutes.

12. The method according to claim 2, wherein the visible light of changing colors produced by the light emitting diodes has a luminosity of about 4,000 millicandelas and the irradiation occurs for about 1 minute to about 5 minutes.

13. The method according to claim 1, wherein the visible light of changing colors produced by the light emitting diodes further passes through a magnetic field downstream of the light emitting diodes, the magnetic field having a magnetic field strength of about 50 µTesla and in addition, being modulated by the magnetic pulses have a field strength of 20 µTesla and frequencies in the range of 120 to 90 kHertz.

14. The method according to claim 2, wherein:
the visible light of changing colors produced by the light emitting diodes is further passes through a magnetic field downstream of the light emitting diodes;
the magnetic field having a magnetic field strength of about 50 µTesla and in addition being modulated by the magnetic pulses have a field strength of 20 µTesla and frequencies in the range of 120 to 90 kHertz.

15. The method according to claim 1, wherein the visible light of the changing colors produced by the light emitting diodes has a luminosity in a range of from 3,000 to 5,000 millicandelas and the irradiation with the visible light occurs for about 1 minute to about 5 minutes.

16. The method according to claim 2, wherein the visible light of the changing colors produced by the light emitting diodes has a luminosity in a range of from 3,000 to 5,000 millicandelas and the irradiation occurs for about 1 minute to about 5 minutes.

17. The method according to claim 1, wherein the one or more active substances, active agents or mixtures thereof are in close association with human serum albumin.

18. The method according to claim 1, wherein one mixture of an active substance and an active agent is added up to seven times to the processed first mixture to obtain the second mixture.

19. The method according to claim 1, wherein more than one mixture of active substances and active agents is added up to seven times to the processed first mixture to obtain the second mixture.

* * * * *